United States Patent [19]

Simons

[11] Patent Number: 5,096,557
[45] Date of Patent: Mar. 17, 1992

[54] INTERNAL STANDARD FOR ELECTROPHORETIC SEPARATIONS

[75] Inventor: Malcolm J. Simons, Fryerstown, Australia

[73] Assignee: Genetype A.G., Zug, Switzerland

[21] Appl. No.: 550,940

[22] Filed: Jul. 11, 1990

[51] Int. Cl.⁵ .......................... C25B 1/00; C25B 7/00; C01D 57/02
[52] U.S. Cl. .............................. 204/182.8; 204/180.1; 204/299 R; 210/748
[58] Field of Search ................ 204/180.1, 182.8, 182.7

[56] References Cited

U.S. PATENT DOCUMENTS 3,607,695 9/1971 Schneider ..................... 204/180 S

OTHER PUBLICATIONS

Carrano, A. et al, *Genomics*, 4:129–136 (1989).
Allen et al, *BioTechniques* 7:736–744 (1989).
Boerwinkle et al, *PNAS* 86:212–216 (1989).
Goldman et al, *Electrophoresis* 3:24–26 (1982).
Marshall, *Electrophoresis* 4:269–272 (1983).
Tegelstrom, *Electrophoresis* 7:226–229 (1987).
Proc. Nat'l Acad. Sci. U.S.A., vol. 86, pp. 212–216 Jan. 1989, by Boerwinkle, Xiong, Fourest & Chan, "Rapid Typing of Tandemly Repeated Hypervariable Loci by the Polymerase Chain Reaction; Application to the Apolipoprotein B3' Hypervariable Region".

*Primary Examiner*—John Niebling
*Assistant Examiner*—Caroline Koestner
*Attorney, Agent, or Firm*—Skjerven, Morrill, MacPherson, Franklin & Friel

[57] ABSTRACT

The present invention provides a method for identifying band positions in an electrophoretic separation. A control is electrophoresed with the sample and serves as an internal control.

7 Claims, No Drawings

INTERNAL STANDARD FOR ELECTROPHORETIC SEPARATIONS

FIELD OF THE INVENTION

The present invention relates to a method for identifying band positions in electrophoretic separations.

1. Background of the Invention

Electrophoresis refers to the migration of charged solutes or particles in a liquid medium under the influence of an electric field. Electrophoretic separations are widely used for analysis of macromolecules. Of particular importance is the identification of proteins and nucleic acid sequences. Such separations can be based on differences in size and/or charge. Electrophoresis can be performed in an unsupported liquid medium (e.g. capillary electrophoresis), but more commonly the liquid medium travels through a solid supporting medium. The most widely used supporting media are gels; e.g. polyacrylamide and agarose gels.

Nucleotide sequences have a uniform charge and are therefore separated based on differences in size. Proteins differ in both size and charge and can be separated based on either property or by a combination of the two. Proteins can be separated based solely on size differences by using sodium dodecyl sulfate (SDS) which gives the protein a uniform charge-to-size ratio.

Non-sieving gels do not impede the flow of molecules and are used for separations based solely on the charge of the species being separated. In isoelectric focusing, species migrate along a pH gradient created in a non-sieving gel until they reach their isoelectric point.

Sieving gels impede the flow of molecules. The pore size of the gel determines the size of a molecule that can flow freely through the gel. The amount of time to travel through the gel increases as the size of the molecule increases. As a result, small molecules travel through the gels more quickly than large molecules and thus progress further from the sample application area than larger molecules. Such gels are used for size-based or size/charge-based separations.

A major problem for clinical applications of electrophoresis is the inherent variability of the process. Much of the variability is due to nonuniform migration through the gels, particularly at the edges of the gels. However, temperature, time, voltage and current also affect the separation. Definitive identification of the separated proteins or nucleotides is often difficult or impossible. Usually a control which includes one or more species of known size (or isoelectric point) is electrophoresed under the same conditions as the samples to provide a marker of known size (or charge) for that gel. For slab gels, usually a control is run at one or both edges of the gel and sometimes also in a central lane in the gel. However, unambiguous identification of the sample molecule frequently cannot be made by lane-to-lane or gel-to-gel comparison, particularly at the edges of the gel.

2. Description of the Prior Art

Preparation and staining of analytical gels is well known. For example, a 3% Nusieve 1% agarose gel which is stained using ethidium bromide is described in Boerwinkle et al, *PNAS* 86:212–216 (1989). Detection of DNA in polyacrylamide gels using silver stain is described in Goldman et al, *Electrophoresis* 3:24–26 (1982); Marshall, *Electrophoresis* 4:269–272 (1983); Tegelstrom, *Electrophoresis* 7:226–229 (1987); and Allen et al, *BioTechniques* 7:736–744 (1989). The method described by Allen et al uses large-pore size ultrathinlayer, rehydratable polyacrylamide gels stained with silver.

Each of the above-described references is incorporated herein by reference in its entirety.

SUMMARY OF THE INVENTION

The present invention provides a method for identifying band positions in an electrophoretic separation. The method comprises electrophoresis of at least one control with the sample as an internal standard. The method can be used for identification of a nucleotide sequence or a protein whether the electrophoretic separation is based on size, charge or a combination thereof. In a preferred embodiment, the control is added directly to the sample prior to sample preparation for loading onto the gel.

DETAILED DESCRIPTION OF THE INVENTION

The present invention provides a method for identifying band positions in electrophoretic separations by electrophoresis of a control with the sample as an internal standard. By adding an internal standard directly to the sample materials, any variables affect both the sample and the control in the same manner. This eliminates ambiguity created by edge effects or other variables associated with the electrophoretic process or conditions.

The methods of this invention are exemplified in terms of separation of proteins and nucleotide sequences. However, the method also applies to electrophoretic separations of other molecules and the present invention is meant to encompass those embodiments.

The present invention contemplates three types of controls for use as internal standards: (1) markers of known size, charge or both in the same size or charge range as the sample analyte; (2) markers having the identical size, charge or both as the sample analyte; and (3) markers that are identical to the sample analyte.

Electrophoretic separations of nucleotides are based on size. For nucleotide sequences, the size correlates directly to the number of nucleotides in the sequence (or the length of the sequence). Electrophoretic separations of proteins can be based on size, on charge or on a combination of the two. However, usually the separation will be based on size (using sieving gels and SDS) or on charge (isoelectric focusing using non-sieving gels), rather than on the combination.

Whatever the type of separation, the first type of internal standard is a control substance that forms a sort of internal ruler against which the sample components can be measured. For size-based analyses, the first type of control is a molecule having a known size. For separations based on charge, the control is a molecule having a known isoelectric point. For separations based on size and charge, the control is a molecule having a known size and isoelectric point. Preferably, a number of molecules of known size and/or charge spanning the anticipated range of the analytes in the sample are combined in a control mixture.

If gene typing produces amplified DNA sequences that differ in length depending on the allele(s) in the sample, a DNA sequence having an intermediate length can distinguish between the two allele sequences. For example, to distinguish between sample nucleotide sequences of 250 nt in one case and 350 in another, a control sequence 300 nt in length can be used. The 350 nt sequence would be located above the control in a gel due to its larger size, and the 250 nt sequence would travel faster and be located below the control. Protein sequences having a molecular weight and/or isoelectric point intermediate between two test substances can function in the same way.

For sample nucleotide sequences, the controls can be a series of nucleotide sequences which span the anticipated sample size range and which differ by known lengths. For example, for sample nucleotide sequences that range in size from 50 to 500 nucleotides, the controls can be a series of nucleotide sequences ranging from 50 to 500 nt and differing by 50 nt in length. For proteins separated by weight, the controls can be a series of proteins that differ in weight by known amounts and cover the expected sample weight range. Similarly, controls having a known range of isoelectric points are used for isoelectric focusing analyses.

The second type of control contains a substance that has the same size, isoelectric point (charge) or both as the sample substance, depending on the type of separation. The control need not be a composition that is identical to the sample analyte. For example, a control for a nucleotide sequence of 300 nt is a nucleotide sequence having the same length. The control need not have the same nucleotide sequence as the sample analyte. A control for a protein with a given isoelectric point and separated by isoelectric focusing is a substance having that isoelectric point. The control substance is preferably a protein.

The third type of control is a substance that is identical to the sample analyte. Therefore, the control includes the protein or nucleotide sequence being analyzed. For example, when attempting to identify human serum albumin (HSA), the control is HSA. When separating human serum proteins, each of the proteins can be present in the control mixture. Alternatively, a portion of the sample can be run with each serum protein separately, or with mixes of two or three of the proteins to identify each of the sample analytes.

When identifying nucleotide sequences associated with alleles of a genetic locus, sequences produced by one or more of the alleles can be used. For example, if one nucleotide sequence is present when a normal beta-globin gene is present in the sample and two smaller sequences are present in a sample associated with sickle cell anemia, either set of nucleotide sequences (normal or disease-associated) or a mixture of all three sequences can be used as the control.

For more complex nucleotide sequence patterns, such as RFLP fragment patterns produced by the alleles of the HLA DQA1 locus, fragment patterns produced by one or a few of the alleles can be added with the sample. When a number of fragments are associated with an allele, a portion of the sample can be added with the fragments for each allele. Fragment patterns from alleles which can be readily distinguished can be pooled to detect a plurality of alleles. In this way, identifying the sample/control mixture in which the sample nucleotide sequences align with the control nucleotide sequences determines the allele(s) present in the sample.

This use of the analyte as an internal standard which is electrophoresed with the sample provides direct identification of a band by observing that the sample analyte aligns with the control in a gel.

The internal standard must be distinguishable from the sample. A suitable way to identify the control will vary depending on the type and sensitivity of the analytical method. Two criteria apply. First, the control must be detectable by the analysis method. Second, the control must differ from the sample in a manner which is readily detected by the analytical method.

For methods where the sample is stained following electrophoresis, the control can be present in the gel in a quantity which is distinguishable from the sample quantity so that the bands produced by the sample and the control are readily identified. Such determinations include ethidium bromide or silver stain for nucleotides or use of Coomassie blue or other dyes for proteins. Determining distinguishable concentrations for controls and analytes is within the level of skill in the art.

For example, for nucleotide sequences stained with ethidium bromide or silver stain, the bands produced by the sequences are detected visually or by optical density. The control nucleotide sequences are preferably present at about one-tenth to one-half of the concentration of the sample nucleotide sequences in the gel. However, for some analysis systems, a control present at ten or more times the concentration of the sample could be readily distinguished from the sample whether the control band is near the sample band or at the same location as the sample band.

For samples which are detected by the presence of a label, the control mixture is also labeled. For example, if radiolabeled proteins or nucleotide sequences are to be separated and detected by autoradiography, the proteins or nucleotides in the control mixture are also labeled with a radionuclide that exposes the film. The sample and control can be at different concentrations. For sample proteins or nucleotides labeled with a dye, enzyme or the like, the controls are also labeled. In such cases, the dye can be the same or different from the sample dye. For example, control proteins can be present in a different amount and labeled with the same dye or the control protein can be labeled with a detectably different dye from that of the sample protein. Differential labeling is well known and includes use of fluorochromes of different colors; use of different enzymes and sequential color development; and use of different dyes for the sample and control.

The control is preferably added to the sample prior to preparation for electrophoresis to minimize any potential differences in treatment. However, addition of the control directly to the sample lane of the gel or other electrophoretic support medium without previous mixing with the sample is also contemplated.

The internal standard is present in a buffer which is compatible with the buffer used in the electrophoresis method. Preferably, the internal standard is in the same buffer as the sample. The concentration of the components of internal standard can vary. Preferably, the concentration provides for ready addition of a small amount of the internal standard to the sample to provide an appropriate final concentration for use in the gel. The internal standard is preferably added to the sample prior to preparation for electrophoresis.

Preparation of the sample for electrophoresis will not differ from prior art preparation when an internal standard is used. The preparation generally includes addition of a composition to make the sample heavier than the electrophoresis buffer (e.g., sucrose or glycerol) and may include a tracker dye (e.g., xylene cyanol for nucleotides bromphenol blue for proteins). For proteins, usually the sample preparation also includes addition of $\beta$-mercapto-ethanol and from 2 to 5% SDS and boiling the sample mixture for about 2 minutes. As stated previously, the internal standard is preferably added to the sample prior to such preparation to minimize differences. However, separate preparation of the internal standard for electrophoresis is also contemplated.

In a preferred embodiment the method is used to determine the HLA allele type for an HLA locus of an individual. The method comprises producing nucleotide sequences characteristic of the HLA allele of said individual from DNA from the individual to produce sample nucleotide sequences. The sample nucleotide sequences are electrophoresed with a control nucleotide sequence characteristic of at least one allele of the HLA locus. The sample nucleotide sequences are compared with said control nucleotide sequence and align with the internal control for the same allele.

This invention is further illustrated by the following specific but non-limiting examples. Temperatures are given in degrees Centigrade and concentrations as weight percentages unless otherwise specified. Procedures that are constructively reduced to practice are described in the present tense, and procedures that have been carried out in the laboratory are set forth in the past tense.

EXAMPLE 1

Analysis of the HLA DQA Locus

The three DR/DQ haplotypes of the HLA DQA1 0102 allele were analyzed as described below. DNA from individuals with each of the three haplotypes was amplified using the polymerase chain reaction (PCR) and then digested with an endonuclease (AluI) to produce three distinctive fragment patterns which correspond to the three haplotypes. The method for producing the amplified DNA sequences and digests is described in detail in a copending application, filed on even date herewith and entitled INTRON SEQUENCE ANALYSIS METHOD FOR DETECTION OF ADJACENT AND REMOTE LOCUS ALLELES AS HAPLOTYPES by Malcolm J. Simons. That application is incorporated herein by reference in its entirety.

The patterns (in base pair sized fragments) were:
1. DR15 DQ6 Dw2: 120, 350, 370, 480
2. DR13 DQ6 Dw19: 120, 330, 350, 480
3. DR16 DQ6 Dw21: 120, 330, 350

Following production, approximately 0.1 µg of "ladder" nucleotide sequences is added to the sample DNA sequences (about 0.5 and 1 µg of DNA). The ladder sequences is a group of nucleotide sequences beginning at 123 bp in length and increasing in length by 123 bp to a final size of about 5,000 bp (available commercially from Bethesda Research Laboratories, Bethesda Md.).

The mixtures of sample and internal standard are electrophoresed using a 4% horizontal ultra-thin polyacrylamide gel (E-C Apparatus, Clearwater Fla.). The bands in the gel were visualized (stained) using silver stain technique [Allen et al, *BioTechniques* 7:736–744 (1989)]. The fragment patterns and the internal standards are readily distinguishable. Use of the internal standard provides ready calculation of the size of the fragments.

The procedure is repeated using a second sample having a DQA1 0102 DR15 DQ6 Dw2 haplotype and a second series of amplifications of a known source of DNA of each of the DQA1 0102-associated haplotypes as controls. One tenth of the amplification reaction mixture is used as an internal standard and added to three aliquots of the sample DNA. The three sample mixtures are electrophoresed on a 6.5% vertical polyacrylamide gel and ethidium bromide stain. The sample sequences align identically with the DQA1 0102 DR15 Dw2 haplotype internal control sequences. In the other two lanes, lighter bands produced by the internal standards are clearly distinguishable from the sample bands.

EXAMPLE 2

Analysis of the pMCT 118 VNTR Locus

DNA from an individual was analyzed to determine which of seven variants of the pMCT 118 VNTR locus (also referred to as the D1S80 VNTR locus) were present in the individual. Variants of the locus can be determined by amplify genomic DNA using a primer pair specific for the locus and determining the length of the resultant amplified DNA sequence. The procedure used for the amplification is the same as that described in Example 1, except that the amplification used thirty cycles of 94° C. for 30 seconds, 65° C. for 30 seconds, and 72° C. for 60 seconds. The sequences of the primers were:

5' GAA ACT GGC CTC CAA ACA CTG CCC GCC G 3'; and

5' GTC TTG TTG GAG ATG CAC GTG CCC CTT GC 3'

The primers hybridize to conserved sequences that flank the pMCT 118 VNTR sequence. Primers having a sequence corresponding to at least 15 consecutive nucleotides of the above described primers can also be used.

Following amplification, the amplified DNA sequences were electrophoresed to determine the variant type. A 2 µl aliquot of the amplification reaction mixture was mixed with an equal volume of an internal standard control.

The internal standard was a mixture of equal amounts of amplification reaction products for each of the 7 VNTR variants prepared under the same conditions using, in each mixture, DNA of a known VNTR variant type. Each of the reaction mixtures were pooled and diluted. The final mixture was a 1:10 dilution of the original concentration of each of the reaction mixtures. The sample was electrophoresed using a 4% horizontal ultra-thin polyacrylamide gel and silver stain as described in Example 1.

The variant types for the tested individual coelectrophoresed with the internal standard and were readily identifiable.

What is claimed is:

1. A method for identifying band positions in an electrophoretic gel separation of a sample comprising
   a. addition of at least one control directly to the sample materials wherein the sample and the control are either unlabeled or have the same label,
   b. electrophoresis of the control with the sample, and
   c. following electrophoretic separation, comparison of the sample materials to the control.

2. The method of claim 1 wherein the sample contains a nucleotide sequence and the control comprises a nucleotide sequence of known size.

3. The method of claim 1 wherein the sample contains a protein and the control comprises a protein of known size.

4. The method of claim 1 wherein the sample contains a protein and the control comprises a protein having a known isoelectric point.

5. The method of claim 1 wherein the control is added directly to the sample prior to sample preparation for electrophoresis.

6. The method of claim 1 wherein said control is present in a concentration from one-tenth to one-half of the sample concentration.

7. A method for determining the HLA allele type for an HLA locus of an individual comprising:

a. producing nucleotide sequences characteristic of the HLA allele of said individual from sample DNA from said individual to produce sample nucleotide sequences;

b. electrophoresis of said sample nucleotide sequences with a control nucleotide sequence characteristic of at least one allele of said locus; and c. comparing said sample nucleotide sequences with said control nucleotide sequence.

* * * * *